(12) United States Patent
Groll

(10) Patent No.: US 8,608,937 B2
(45) Date of Patent: Dec. 17, 2013

(54) BIOSENSOR WITH PREDETERMINED DOSE RESPONSE CURVE AND METHOD OF MANUFACTURING

(75) Inventor: Henning Groll, Oro Valley, AZ (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 996 days.

(21) Appl. No.: 12/413,778

(22) Filed: Mar. 30, 2009

(65) Prior Publication Data

US 2010/0243441 A1    Sep. 30, 2010

(51) Int. Cl.
*G01N 27/327*    (2006.01)

(52) U.S. Cl.
USPC .............. 205/777.5; 205/792; 204/403.01

(58) Field of Classification Search
USPC ............. 204/403.01–403.15; 205/777.5, 778, 205/792; 435/4–40.52
See application file for complete search history.

(56) References Cited

U.S. PATENT DOCUMENTS

| | | | |
|---|---|---|---|
| 5,384,028 A | 1/1995 | Ito | |
| 5,431,800 A | 7/1995 | Kirchhoff et al. | |
| 5,762,770 A | 6/1998 | Pritchard et al. | |
| 6,582,573 B2 | 6/2003 | Douglas et al. | |
| 6,599,406 B1 | 7/2003 | Kawanaka et al. | |
| 6,814,844 B2 | 11/2004 | Bhullar et al. | |
| 7,312,042 B1 | 12/2007 | Petyt et al. | |
| 7,829,023 B2* | 11/2010 | Burke et al. | 422/82.01 |
| 2001/0052470 A1* | 12/2001 | Hodges et al. | 205/775 |
| 2003/0186263 A1 | 10/2003 | Frey et al. | |
| 2004/0072364 A1* | 4/2004 | Tisone et al. | 436/180 |
| 2004/0124098 A1 | 7/2004 | Huang et al. | |
| 2004/0194302 A1* | 10/2004 | Bhullar et al. | 29/847 |
| 2005/0016845 A1 | 1/2005 | Groll et al. | |
| 2005/0103624 A1 | 5/2005 | Bhullar et al. | |
| 2005/0178663 A1 | 8/2005 | Kobayashi | |
| 2006/0144704 A1 | 7/2006 | Ghesquiere et al. | |
| 2006/0200981 A1* | 9/2006 | Bhullar et al. | 29/847 |
| 2007/0170054 A2* | 7/2007 | Wilsey | 204/403.01 |
| 2008/0060196 A1 | 3/2008 | Wang et al. | |
| 2008/0066305 A1 | 3/2008 | Wang et al. | |

FOREIGN PATENT DOCUMENTS

| | | |
|---|---|---|
| DE | 103 43 477 A1 | 7/2004 |
| WO | WO 2006/042304 A1 | 4/2006 |

OTHER PUBLICATIONS

International Search Report and Written Opinion of the International Searching Authority; PCT/EP2010/001857; Jun. 17, 2010.

* cited by examiner

*Primary Examiner* — Susan D Leong
(74) *Attorney, Agent, or Firm* — Bose McKinney & Evans LLP

(57) ABSTRACT

The present invention provides a system of biosensors whose dose-response curves are maintained within a predetermined and desired range or tolerance during production by selecting a feature of the biosensors that can be varied during production. For example, in one exemplary embodiment the effective area of the working electrode of an electrochemical biosensor can be varied during production as needed to offset variations that occur, e.g., in the reagent of the biosensors as production proceeds. In another exemplary embodiment, the dose-response curve of biosensors not yet produced can be predicted and one or more features of these biosensors can be selected to maintain the dose-response curve within a predetermined range or tolerance.

9 Claims, 14 Drawing Sheets

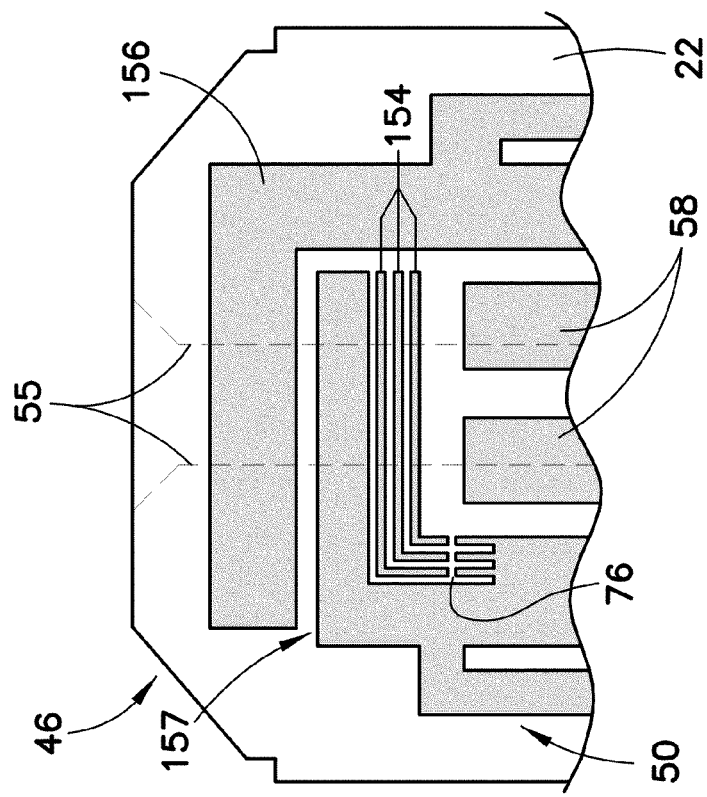
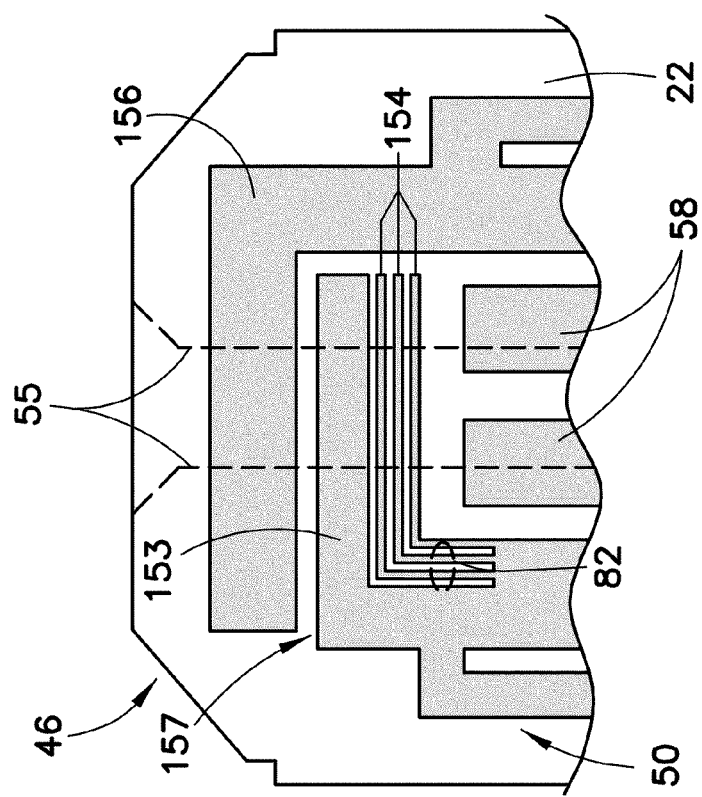
FIG. 3C
FIG. 3D

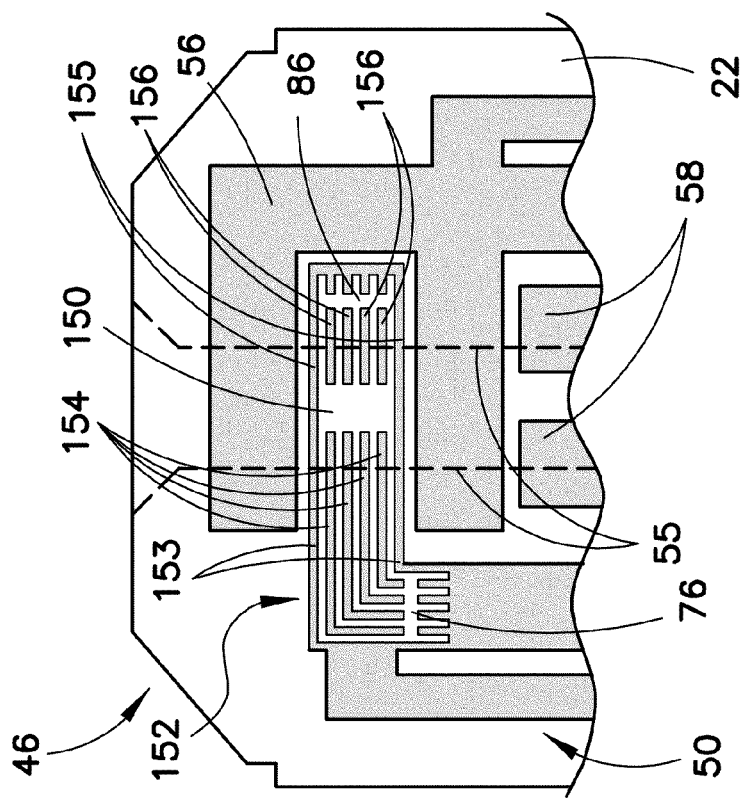
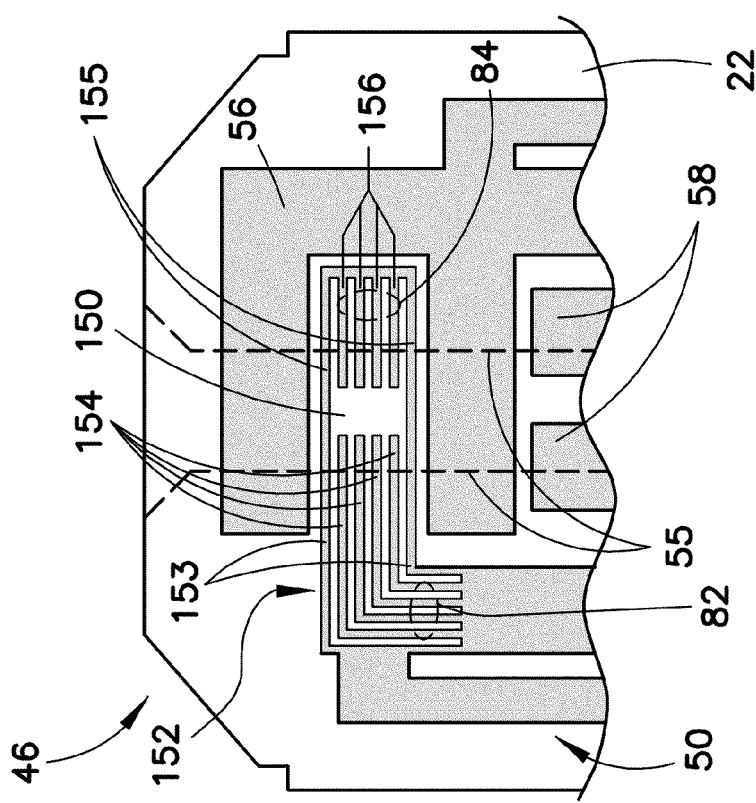

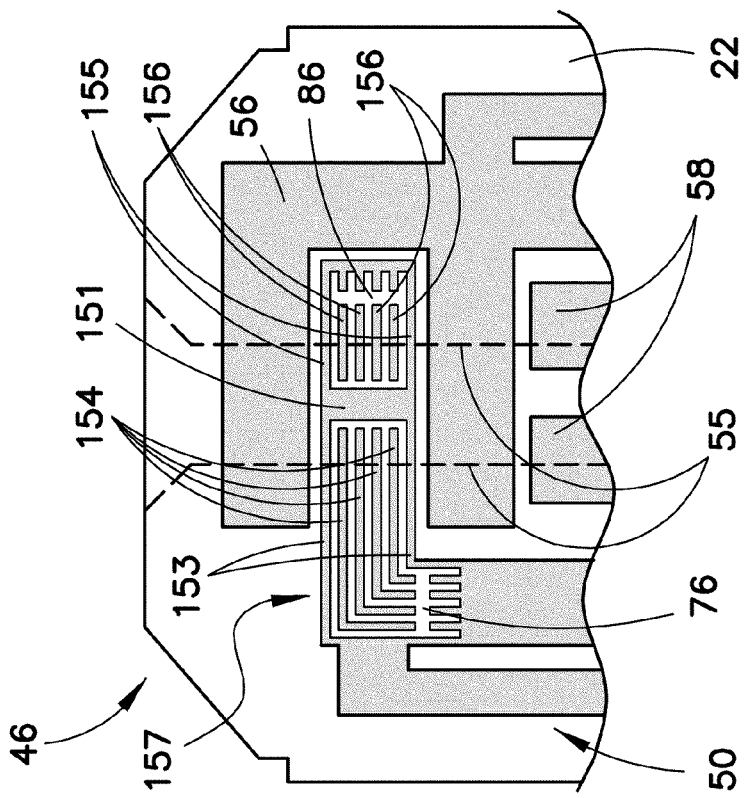
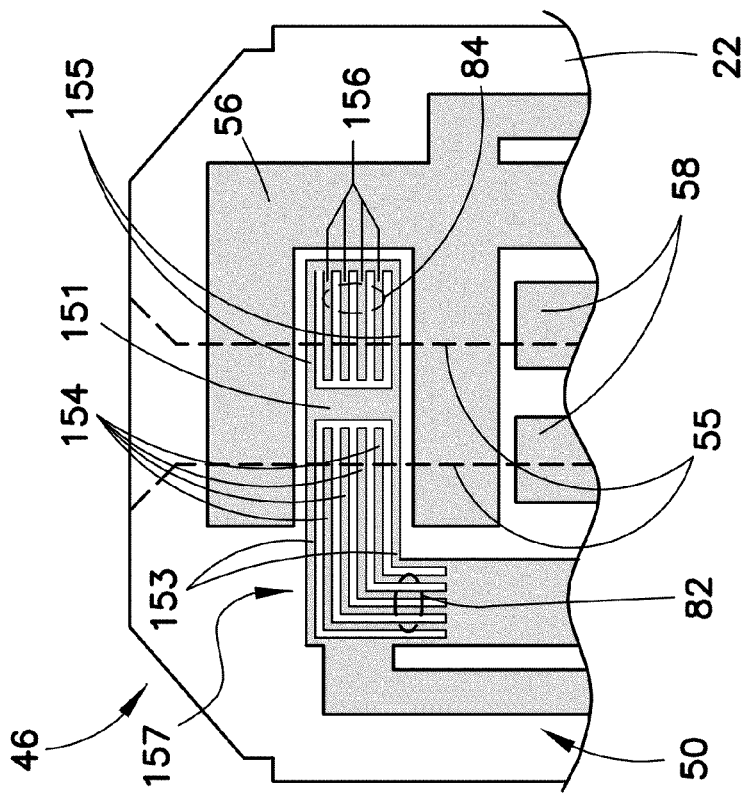

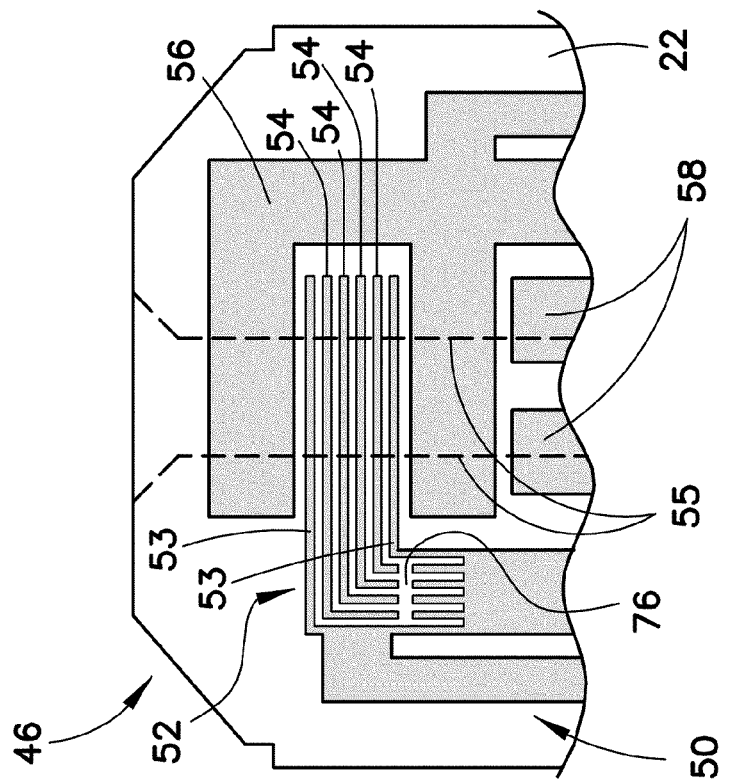
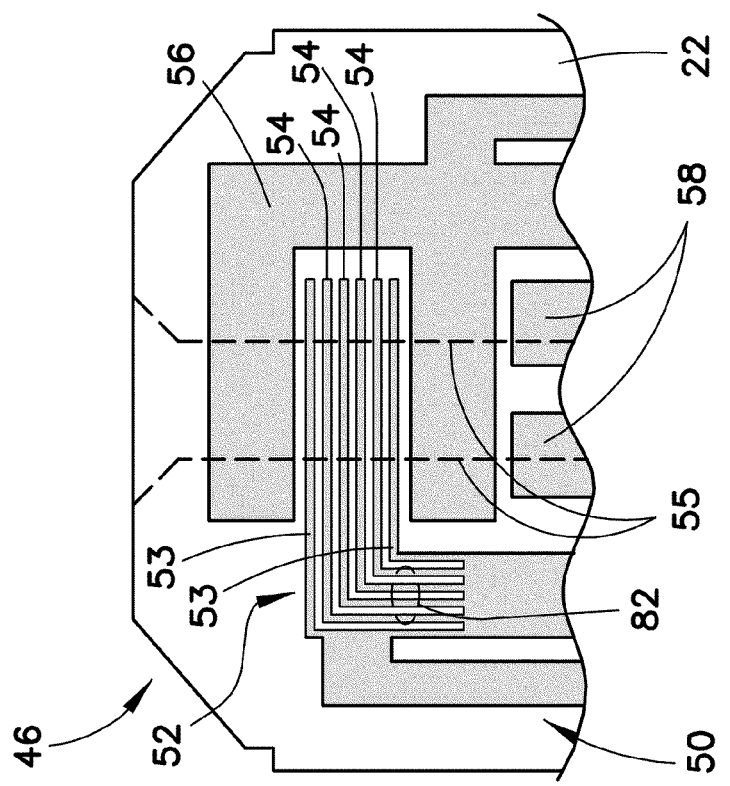

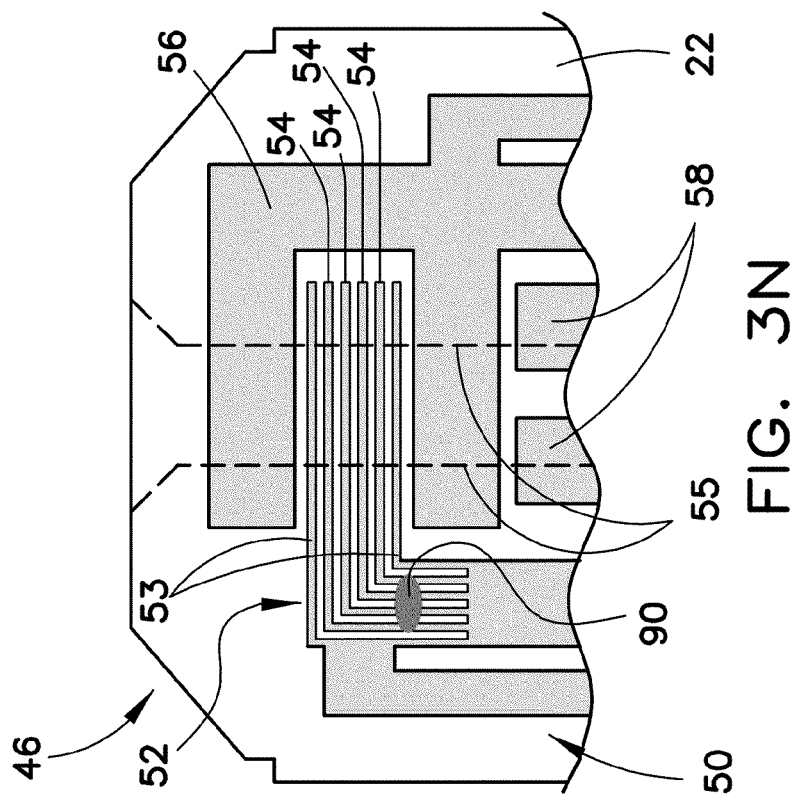
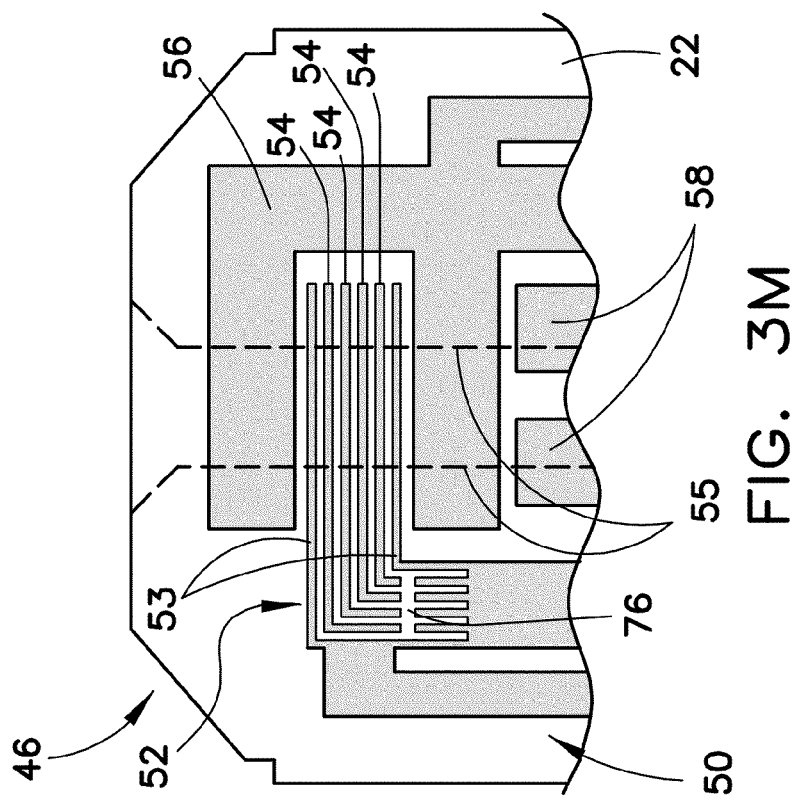

BIOSENSOR WITH PREDETERMINED DOSE RESPONSE CURVE AND METHOD OF MANUFACTURING

BACKGROUND

The present invention relates to biosensors for use in measuring concentration of analytes in biological fluids, and more particularly, to variations in the dose-response curves of such biosensors that occur during production.

Measuring the concentration of substances in biological fluids is important for diagnosis and treatment of many medical conditions. For example, the measurement of glucose in body fluids, such as blood, is crucial to the effective treatment of diabetes. Multiple methods are known for determining the concentration of analytes in a blood sample and generally fall into one of two categories: optical methods and electrochemical methods.

Optical methods generally involve spectroscopy to observe the spectrum shift in the fluid caused by concentration of the analyte, typically in conjunction with a reagent that produces a known color when combined with the analyte.

Electrochemical methods generally rely upon the correlation between a current (amperometry), a potential (potentiometry) or accumulated charge (coulometry) and the concentration of the analyte, typically in conjunction with a reagent that produces charge-carriers when combined with the analyte. See, for example, U.S. Pat. No. 4,233,029 to Columbus, U.S. Pat. No. 4,225,410 to Pace, U.S. Pat. No. 4,323,536 to Columbus, U.S. Pat. No. 4,008,448 to Muggli, U.S. Pat. No. 4,654,197 to Lilja et al., U.S. Pat. No. 5,108,564 to Szuminsky et al., U.S. Pat. No. 5,120,420 to Nankai et al., U.S. Pat. No. 5,128,015 to Szuminsky et al., U.S. Pat. No. 5,243,516 to White, U.S. Pat. No. 5,437,999 to Diebold et al., U.S. Pat. No. 5,288,636 to Pollmann et al., U.S. Pat. No. 5,628,890 to Carter et al., U.S. Pat. No. 5,682,884 to Hill et al., U.S. Pat. No. 5,727,548 to Hill et al., U.S. Pat. No. 5,997,817 to Crismore et al., U.S. Pat. No. 6,004,441 to Fujiwara et al., U.S. Pat. No. 4,919,770 to Priedel, et al., and U.S. Pat. No. 6,054,039 to Shieh, which are hereby incorporated in their entireties.

Electrochemical biosensors for conducting tests are typically provided as a disposable test strip having a reagent thereon that chemically reacts with the analyte of interest in the biological fluid. The test strip is mated to a test meter such that the test meter can measure the reaction between the analyte and the reagent in order to determine and display the concentration of the analyte to the user.

The response of an electrochemical biosensor to a potential step is largely governed by the Cottrell equation (F. G. Cottrell, Z. Physik. Chem., (1902)), Equation (1), below.

$$I = \frac{nFAD^{\frac{1}{2}}}{\pi^{\frac{1}{2}} t^{\frac{1}{2}}} C \qquad (1)$$

where
n—number of electrons per molecule of analyte
F—Faraday Constant
A—working electrode area
D—diffusion coefficient
t—time after application of potential step
C—Analyte concentration It can be appreciated from Equation (1) that a change in the diffusion coefficient D will lead to a change in the dose-response of the sensor.

In many electrochemical sensors, dried films of chemistry are employed, typically covering the working electrode or the working and counter electrodes. These dried films contain enzymes that aid the exchange of electron(s) between the analyte and a mediator. A chemical process takes place when a liquid sample such as blood containing the analyte of interest hydrates the film. During this process, the film swells, analyte molecules diffuse into the film, and, with the aid of the analyte-specific enzymes present in the film, electron(s) are exchanged with the mediator molecules. In the presence of a specifically applied or controlled electrical potential, the mediator molecules diffuse to the electrode surface and are reduced or oxidized. Resulting current is then measured and then correlated using known techniques (e.g. amperometry, coulometry, potentiometry, voltammetry) to an amount, concentration or other desired characteristic of the analyte.

What is set forth as a simple diffusion coefficient D in Equation (1) actually (a) changes over time due to, e.g., swelling of the reagent; (b) is a sum of multiple diffusion processes (e.g., analyte diffusing from the fluid sample into the film to the enzyme, mediator diffusing from the reaction center to electrodes, etc.); and (c) may need to be adjusted to account for the kinetics of the enzyme reactions.

For the purposes of illustration, the following simple linear dose response equation (Equation (2)) can be used:

$$C = k_{BC} I_{BC} + k I_t \qquad (2)$$

where
$k_{BC}$, $k$ are system specific coefficients
$I_{BC}$ is analyte independent blank current
$I_t$ is current measured at time t
Or, in terms of current densities, introducing the working electrode area A:

$$C = k_{BC} A j_{BC} + k A j_t \qquad (3)$$

where
$j_{BC}$—analyte independent blank current density
$j_t$—current density at time t
In the case of a very small blank current, Equation (3) can be simplified to $$C = k A j_t \qquad (4)$$

The analyte concentration C can be inaccurately estimated by an amount $\Delta C$, which results from a change $\Delta k$ that is in turn caused by, for example, variations in composition or thickness of the chemistry film that occur as part of an ongoing production process. This problem of inaccurately estimating analyte concentration can be appreciated from Equation (5), below.

$$C + \Delta C = (k + \Delta k) A j_t \qquad (5)$$

Since variations in composition and thickness of the chemistry film used in these biosensors are important contributors to inaccuracy of the analyte concentration estimation, these parameters are typically controlled very well during the production process of an electrochemical biosensor. Nonetheless, in typical manufacturing processes, batches of only limited size can be produced based on, e.g., limited sized batches of raw materials that are used to produce the final biosensor product. In many cases, a new lot of biosensors might have a significantly different k, and a lot-to-lot variation as quantified in Equation (5) will thus result. Also, longer term trends, such as wear of machine parts or changes in raw material composition might also lead to a change of k, again resulting in an incorrect slope of the dose-response curve.

A standard method known in the art to address variations in the system specific coefficient k is to provide a lot specific coefficient $1-\Delta m$ that counteracts the change induced by $\Delta k$. This is represented in Equations (6) and (7), below:

$$C=(k+\Delta k)(1-\Delta m)Aj_t \quad (6)$$

With $$\Delta m = \frac{\Delta k}{k+\Delta k} \quad (7)$$

Often, pairs of lot specific coefficients are provided, a first one of the coefficients describing the slope, similar to $1-\Delta m$, and the second describing the intercept of a linear dose-response curve. Several lot specific coefficients or pairs of coefficients can be stored in the measurement instrument that is used with the biosensor and then selected by the user or automatically selected based on information contained on the biosensor. This approach has the drawback of requiring the meter to have sufficient memory to store several correction coefficients and in some cases also undesirably relies upon the user to select the correct lot information. It is known that users of these devices can fail to perform such required steps.

Alternatively, another common practice known in the art involves downloading such correction or calibration information into the test meter from an electronic read-only memory key (ROM key) that is inserted into a socket of the test meter. See, e.g., U.S. Pat. No. 5,366,609. Because this calibration data may only be accurate for a particular production lot of test strips, however, the user is usually asked to confirm that the lot number of the test strip currently in use matches the lot number for which the ROM key was programmed. This method undesirably requires production of several different ROM keys, and also relies on the user to change the ROM key when using a new vial of biosensors, which has been found does not always occur.

Yet another known method is to provide the value of the correction coefficients to the measurement instrument via a code key or via the disposable container (e.g., barcode). Another variant involves coding each biosensor itself with a barcode or other coding information. In this method, when the coded biosensor is inserted into the meter, the meter automatically applies the correct correction coefficients from several that are stored in its memory. While obviating the need for the user to take any affirmative steps to ensure that the proper correction coefficients are being used, this method requires that the meter have stored in it all correction coefficients that correspond to the various codes that can be provided on multiple different lots of biosensors, and of course requires lot specific coding of the biosensors.

Still another method involves controlling the biosensor production process so that only negligible lot-to-lot variations ($\Delta k$) occur, and if needed, those biosensors not meeting the implicit $\Delta k \approx 0$ requirement are rejected and discarded. This is often referred to as "universal code". However, such methods are costly due to the large costs of meeting tight tolerances imposed in the first instance, and can be wasteful when large quantities of biosensors must be rejected and discarded for failing to meet those tolerances. Such wastefulness can be avoided by saving the biosensors of the rejected lots and providing them with another meter that requires a specific code input from the user, strip or vial, i.e. non-universal code meters. However, this requires that multiple lines of meter products are produced and distributed, which requires additional costs and expenses.

Because of the large amount of waste and difficulty in meeting tolerances, the "brute force" method just discussed is largely believed by those skilled in the art to be economically unworkable on a large production scale. Instead, those of skill in the art have come to accept the now conventional wisdom that lot to lot variations in the dose-response curve are inherent in the large-scale production of biosensors, and some type of calibration scheme like those discussed above must therefore be implemented after production in order to ensure an accurate estimation of the analyte concentration in a sample.

It would be desirable to provide another method for adjusting for variations in the dose-response curve of biosensors.

SUMMARY OF THE INVENTION

The present invention departs from the conventional wisdom noted above and provides a system of biosensors whose dose-response curves are maintained within a predetermined and desired range during production by selecting a feature of the biosensors that can be varied during production. Once production of these inventive biosensors is completed, calibration is unnecessary.

In one form thereof, the present invention provides a method of manufacturing biosensors. In this method, at least first and second biosensors of the same model, and typically many more, are produced. The dose-response curve of the first biosensor is determined, typically by dosing it with a quality control solution during its manufacture and then measuring the response. Based upon the response, a feature of the second biosensor, and typically many more biosensors, is determined. That feature is then implemented into production of the second and successive biosensors, such that the dose-response curve of the second and subsequent biosensors is within the predetermined range.

In one exemplary embodiment, the biosensors are electrochemical biosensors and the feature that is determined is the size or effective area of the electrical pattern of the biosensors. In this embodiment, the method involves adjusting the effective area of the electrical pattern of the second biosensor to bring the dose-response curve of the second biosensor within the predetermined range. For example, the electrical pattern may comprise a working electrode having several fingers that can be electrically disconnected during production, such as by severing the fingers with a laser, and this in turn brings the dose-response of the biosensors to within a predetermined range. In certain embodiments, such severing effectively disconnects a portion of the working electrode that is exposed in the sample receiving chamber.

While the effective area of the working electrode exposed in the sample receiving chamber is one advantageous feature that can be adjusted, and detailed disclosures and examples of the same are provided hereinbelow, it is envisioned that one of skill in the art could employ these teachings to determine and adjust other features of biosensors during production to bring their dose response curves to within a predetermined range. For example, adjustment of the "excitation voltage" in an amperometric biosensor could be made by providing a resistor, current or voltage divider in the conductive trace leading to the working electrode. In one form, the electrical pattern that includes the conductive trace and the working electrode may be initially formed with an 'open' or severed portion which, once the required dose response adjustment is determined, can be 'closed' or connected with a conductive material known electrical characteristics that provide the desired adjustment.

In another form thereof, the present invention provides a system of electrochemical biosensors comprising first and second biosensors of generally the same model. The first biosensor has a first electrical pattern and the second biosensor has a second electrical pattern. The first and second electrical patterns have different effective areas, and the dose-response curves of the first and second biosensors are within the same predetermined range.

In this embodiment, the effective area of the electrical patterns is a feature of the biosensors that can be adjusted during production, as needed, to maintain the dose-response of the biosensors within a predetermined range or tolerance. In one exemplary embodiment, the working electrodes of the biosensors comprise multiple fingers. Some or all of the fingers, or portions thereof, can be electrically disconnected to offset production variations and thus maintain the dose-response curve within a predetermined and accepted range or tolerance.

Embodiments incorporating the present invention advantageously avoid the need for the meter and/or user to calibrate the biosensors before the user uses them to measure analyte concentration.

BRIEF DESCRIPTION OF THE DRAWINGS

The above-mentioned aspects of the present invention and the manner of obtaining them will become more apparent and the invention itself will be better understood by reference to the following description of the embodiments of the invention, taken in conjunction with the accompanying drawings, wherein.

Corresponding reference numerals are used to indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

These teachings provide a system of biosensors in which multiple substantially identical biosensors of the same model are provided or produced, and in which one feature of the biosensors, such as the effective area of the electrical pattern, is varied during production in order to maintain the dose-response curves of all biosensors produced within a predetermined range or tolerance.

For purposes of this specification, the term "effective area" should be construed broadly, and typically refers to the size of an electrical feature, such as an electrode, through which electricity can be conducted when the biosensor is connected to a meter or otherwise provided with electricity. In many cases, the effective area will be substantially determined by the surface area of the electrical feature, which may be appropriate in the case of a substantially flat biosensor having a thin, flat electrical pattern formed on or in such biosensor. In other applications, effective area can be a function of whether specific electrical features are electrically connected to other features of the electrical pattern. Still in other applications, effective area may be a function of thickness or volume of a specific electrical feature. In exemplary embodiments, effective area comprises the surface area of the working electrode that is located in the sample receiving chamber and is also electrically connected to the meter electronics.

The term "dose-response curve" as used herein broadly describes experiments or testing in which fluid samples having a concentration of a particular analyte (or multiple analytes) are deposited in or on a biosensor, and the biosensor measures a current, charge, potential, resistance, color, or some other parameter that can be correlated to the concentration of analyte in the fluid sample. The "dose" thus refers to the concentration of analyte and the "response" refers to the measured parameter that corresponds to such concentration. The term "concentration-response curve" is also known in the art and is synonymous herein with "dose-response curve."

Figure 1A:
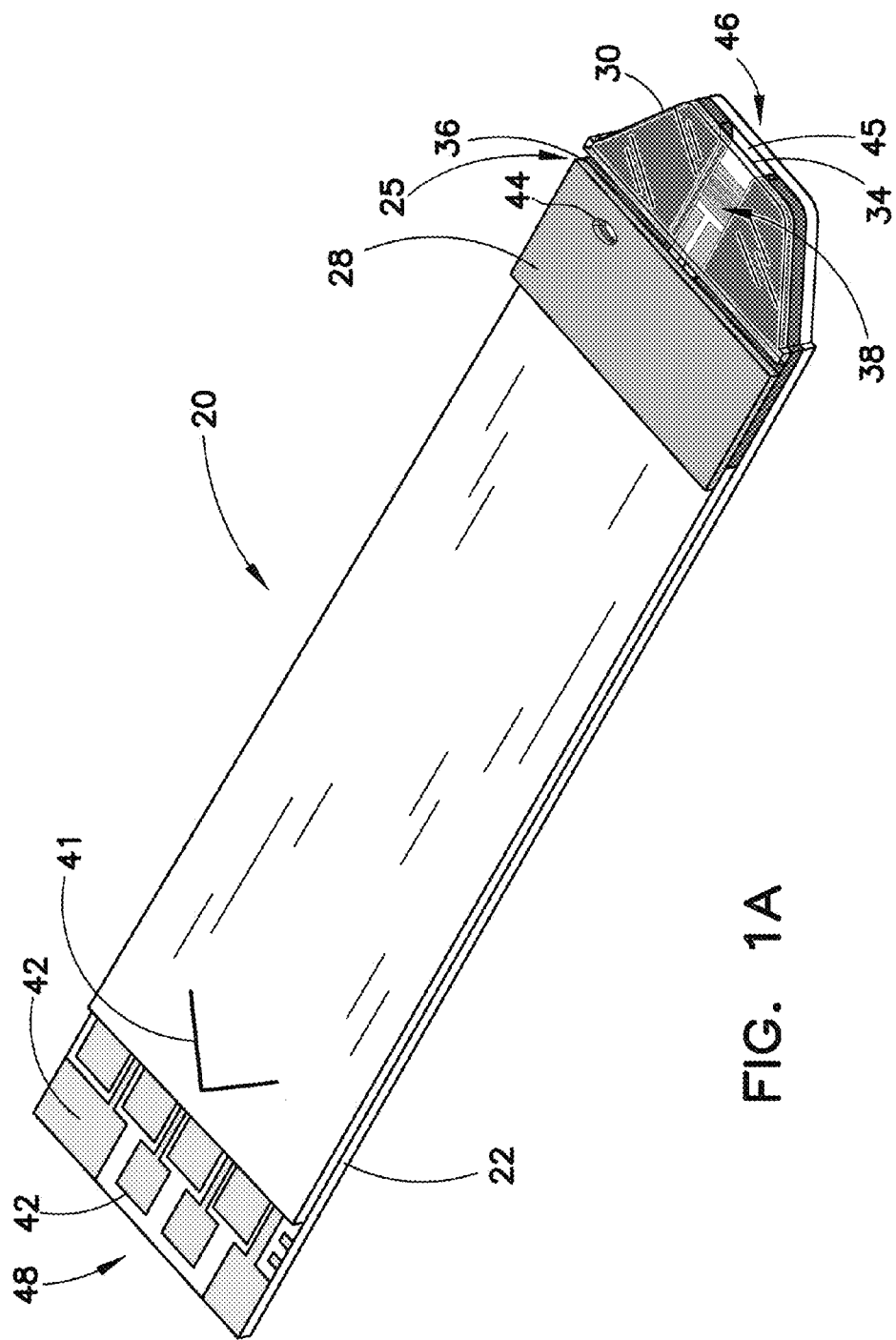
FIG. 1A is a perspective view of a biosensor formed in accordance with these teachings.
Figure 1B:
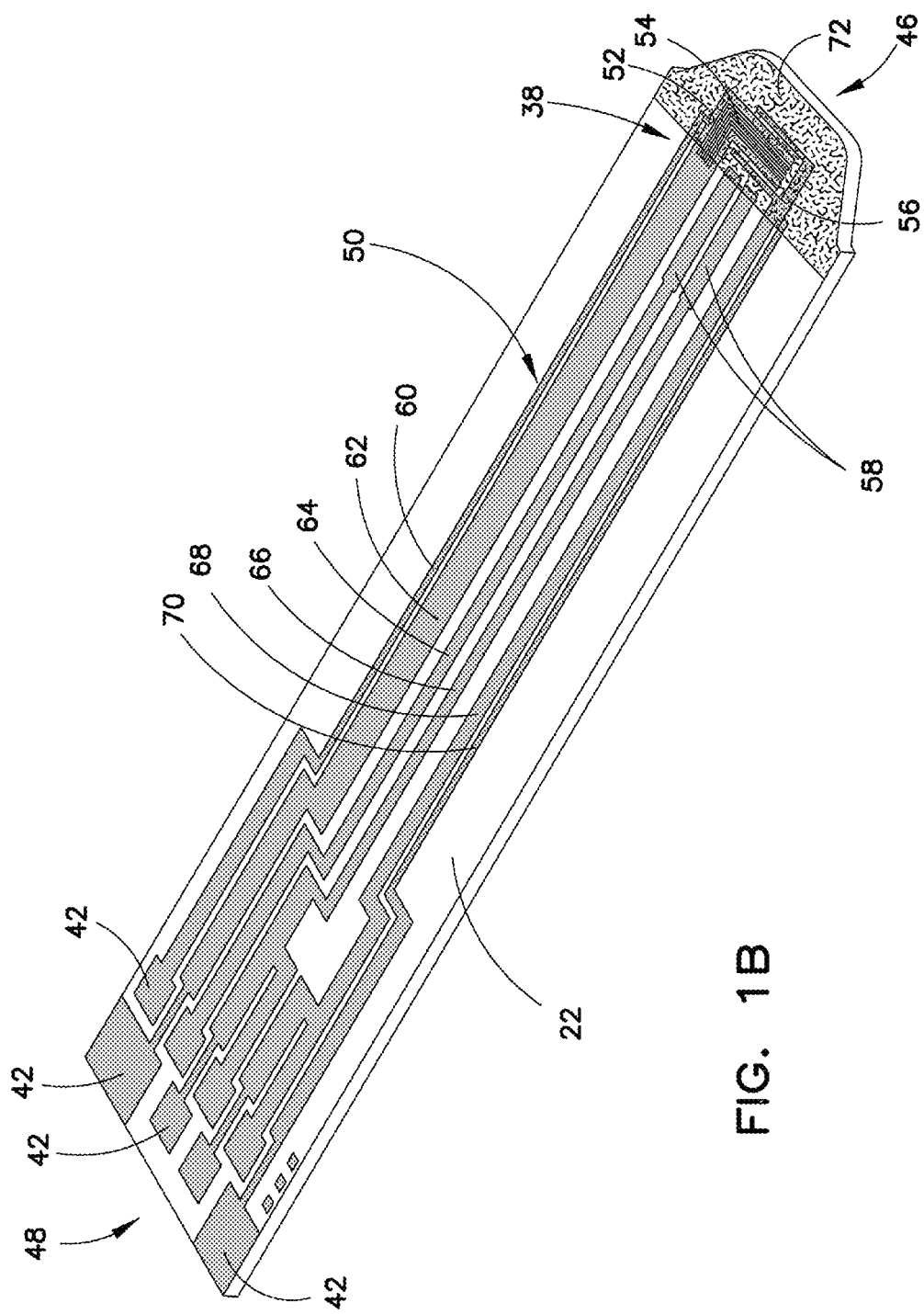
FIG. 1B is a perspective view of a substrate of the biosensor shown in FIG. 1A having an electrical pattern formed thereon.
Figure 2:
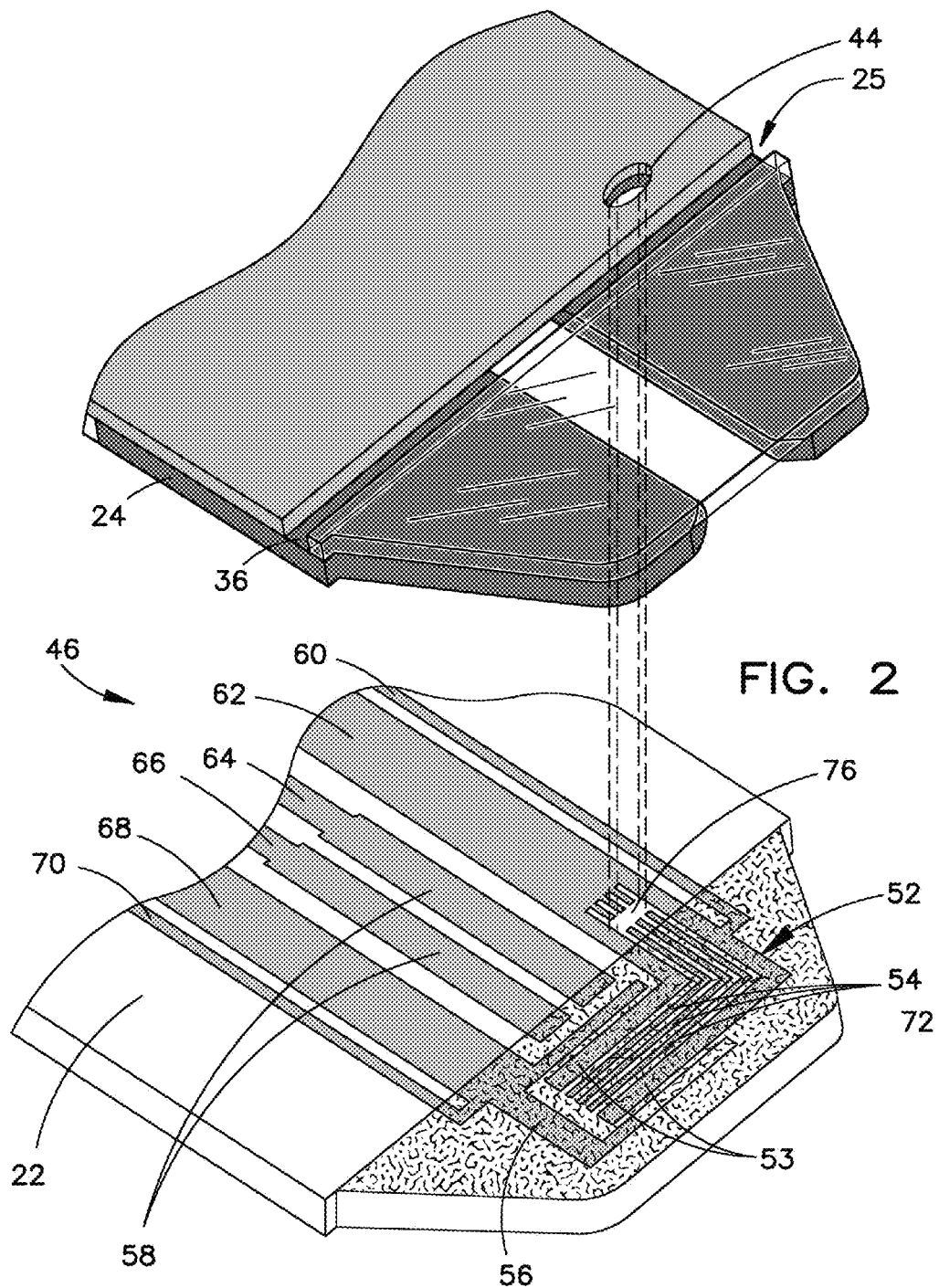
FIG. 2 is a fragmentary exploded perspective view of a portion of the biosensor and substrate shown in FIGS. 1A and 1B.

Turning now to FIGS. 1A, 1B, and 2, there is shown one representative "model" of a biosensor 20 useful in accordance with the present teachings, although one of skill in the art will readily recognize that these teachings may be incorporated into a virtually endless variety of biosensor models, and indeed, have applicability in other devices. Biosensor 20 includes a base substrate 22, a spacing layer 24, and a covering layer 25 comprising body cover portion 28 and chamber cover portion 30. The spacing layer 24 and the covering layer 25 cooperate to define a sample-receiving chamber 34 extending between the base substrate 22 and at least the chamber cover portion 30 of the covering layer 25. A gap 36 is provided between body cover 28 and chamber cover 30, which defines a vent opening communicating with the sample-receiving chamber 34 to allow air to escape the chamber as a sample fluid enters the chamber from the edge opening or fluid receiving opening 45. In an alternate embodiment, the covering layer could comprise a single top cover (not shown) overlying the spacing layer 24 and including a vent hole (not shown) in fluid communication with the sample receiving chamber.

Biosensor 20 includes a dosing end 46 and a meter insertion end 48. The dosing end can be configured to be distinguishable from the meter end so as to aid users. For example, dosing end 46 of biosensor 20 shown in FIG. 1 is bevelled and also is provided with a color that contrasts with the remainder of the biosensor. Strip graphics such as arrow 41 can also be used to indicate the direction of insertion of the biosensor into the meter.

In one aspect of these teachings, although the effective area of the electrical patterns or other feature may be varied on a lot to lot or other basis, the overall "look and feel" of the biosensors from each model will typically be the same and indistinguishable to the user. For example, the strip graphics, colored dosing end, cover layer 25, spacing layer 24, and shape and size of the biosensor would typically all be identical or substantially identical among all biosensors of a given model, even though some of the biosensors have a feature that has been varied during production to maintain the dose-response curve within a desired tolerance. In other embodiments, however, it may be desirable to change certain features of individual biosensors within a particular model, such as color, graphics or the like. Examples of "models" of biosensors, as that term is used herein, include but are not limited to Accu-Chek® Comfort Curve® brand test strips or biosensors, and Accu-Chek® Aviva brand biosensors or test strips.

Turning to FIG. 1B, base substrate 22 carries an electrical pattern 50 thereon having electrical features 38. Portions of the electrical features 38 can also be seen in FIG. 1A in chamber 34. Electrical pattern 50 is formed on substrate 22 by, e.g., laser ablation, as described in U.S. Publication No. 20050103624, the disclosure of which is hereby incorporated herein by reference. Other suitable means for forming electrical pattern 50 include laser scribing, screen printing and other techniques known in the art. Other electrical features 38 of electrical pattern 50 include working electrode 52, which further comprises a series of fingers 54, a forked counter electrode 56, dose sufficiency electrodes 58, and a series of traces 60, 62, 64, 66, 68 and 70, all of which lead from one or more respective electrical features 38 to various contact pads 42 for electrical communication with a meter in which the biosensor is inserted. A reagent layer or film 72 is applied at the dosing end 46 of substrate 22, and may be applied to the biosensor by any number of methods, many of which are described in previously cited U.S. Publication No. 20050016844. Additional basic design and functional details of an electrochemical biosensor having the basic features just noted can be found in U.S. Publication No. 20050016844, the disclosure of which is hereby incorporated herein by reference.

Referring to FIG. 2, dosing end 46 of biosensor 20 is shown in perspective with spacing layer 24 and a two-piece covering layer 25 exploded away. A small access opening 44 is provided through cover layer 25 and spacer layer 24 and is positioned in the assembled biosensor immediately over severed area 76 as indicated by dashed lines. Opening 44 allows a laser or other tool to access a portion of some of the fingers 54 of working electrode 52 at the adjustment section 82 (FIGS. 3A-3N) and sever them as shown, leaving the severed area 76, and effectively electrically isolating or disconnecting one or more of the fingers 54, which thereby changes the effective area of the electrical pattern to a desired degree, particularly the working electrode. As shown, e.g., three fingers 54 of the working electrode 52 are severed, leaving only two larger fingers 53, thereby reducing the effective area of the working electrode 52 exposed within the chamber 34 by a factor of about 33%, assuming that fingers 53 are each individually as wide as the sum total width of all three fingers 54 combined.

The effect of adjusting the effective area of the working electrode is to maintain the dose-response within a desired tolerance. This can be understood from again reviewing Equation (5) that was discussed above.

$$C+\Delta C=(k+\Delta k)Aj_t \tag{5}$$

As can be appreciated, the measured or estimated analyte concentration is not only proportional to the constant k, but also A, which is the area of the working electrode. Thus, a change $\Delta k$ resulting from lot to lot variations can be offset by a respective change $\Delta A$, as indicated in equation (8), below.

$$C=AC=(k+\Delta k)(A-\Delta A)j_t \tag{8}$$

Or, expressed in terms of $\Delta A$, Equation (9) provides:

$$\Delta A = \frac{\Delta k}{k+\Delta k}A \tag{9}$$

Thus, by determining $\Delta k$, which can be done, e.g., by testing an individual biosensor with a control solution of known analyte concentration, the required change in area, if any, of the working electrode can be determined from equation (9). As described in further detail below, this adjustment in area can be done as one of the final steps in a biosensor manufacturing process, or it can be done on a prospective basis and incorporated into an earlier stage of the production process during which the electrical patterns are formed on the substrates.

If the effective area of the electrical pattern of the biosensor is to be adjusted during a later production stage, e.g., after the biosensors are already essentially formed, the system in accordance with these teachings may provide various options for making the adjustment.

As alluded above, in certain exemplary embodiments, the "effective area" to be adjusted comprises the surface area of the working electrode that is located in the sample receiving chamber. In these embodiments, to provide the range of adjustability with respect to the dose response curve, the working electrode may typically be provided with a basic portion that is the same in all biosensors of a given model. The working electrode may also include several other fingers that can be selectively severed to alter the dose response curve.

Figure 3A:
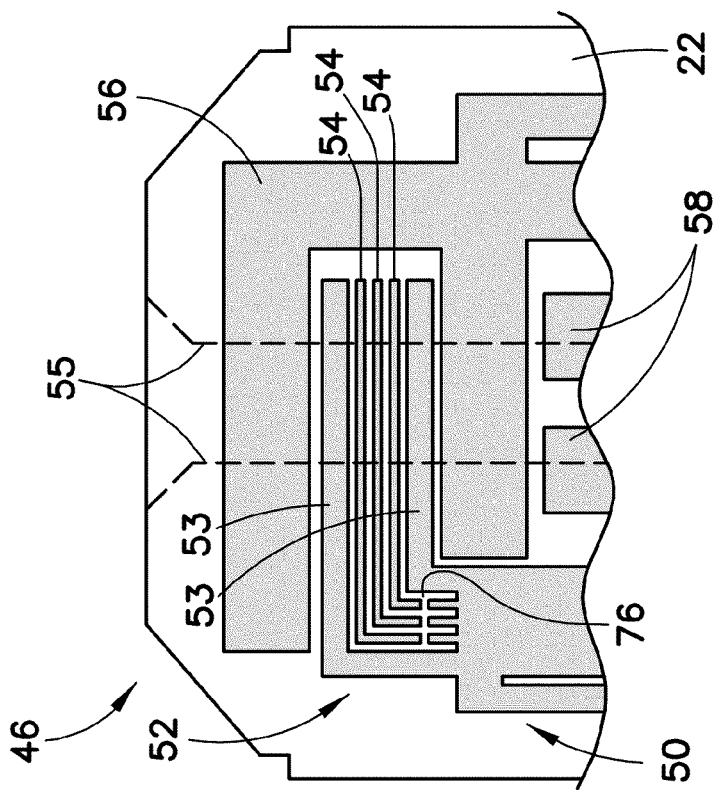
FIGS. 3A-3N are fragmentary plan views of various dosing ends of biosensor substrates having an electrical pattern formed thereon whose working electrode effective area can be altered in accordance with these teachings.
Figure 3B:
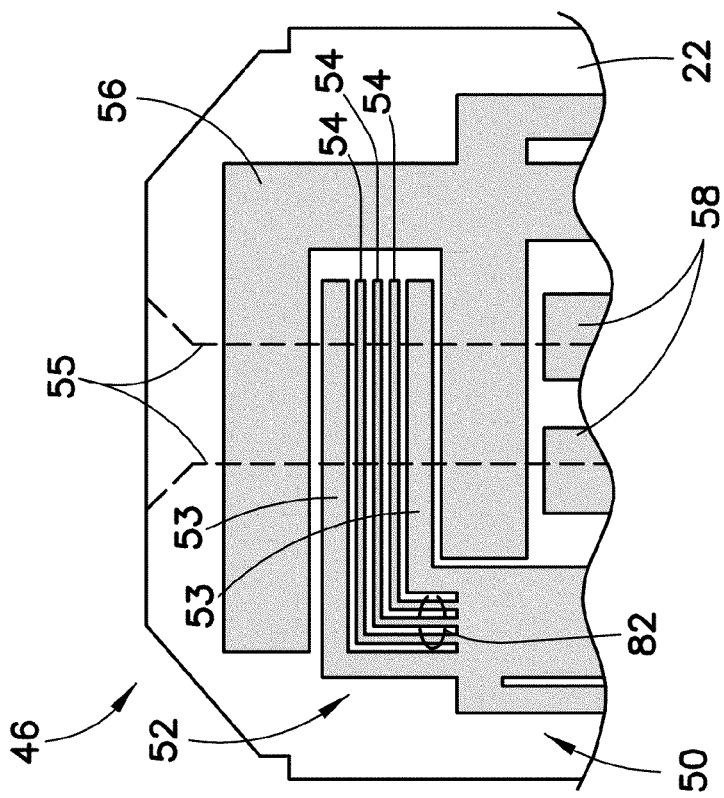

For example, FIGS. 3A and 3B depict an exemplary embodiment of a dosing end 46 of a substrate 22 suitable for use in the system of biosensors in accordance with these teachings. (Dosing end 46 is also shown in FIGS. 1 and 2.) An electrical pattern 50 is provided having a working electrode 52 that further comprises a series of adjustment fingers 54, permanent fingers 53 that are wider than fingers 54, a counter electrode 56, and dose sufficiency electrodes 58. The capillary space or sample receiving chamber is shown at reference numeral 55 as a dashed line, and a reagent film or layer (not shown in FIGS. 3A-3N) is typically present in at least a portion of this capillary space at least in contact with the working electrode 52, as discussed above with reference to FIGS. 1 and 2.

In this exemplary embodiment, permanent fingers 53 of working electrode 52 provide approximately 80% of the nominal value of the area of the working electrode that is located in the sample receiving chamber. By contrast, fingers 54 of working electrode 52, which extend into the capillary and are selectively severable, provide an additional approximately 40% of the nominal value. As a result, in this particular embodiment, the dose response curve can be adjusted between up to about 120% of the nominal working electrode area (all fingers 54 unsevered) or down to 80% (all fingers 54 completely severed). Of course, one of skill in the art would readily recognize that the percentages just noted can be varied as desired by, e.g., providing fingers 53 and/or 54 wider or narrower, and/or providing more of less than the three selectively severable fingers 54. A working electrode effective area that may be varied between about 80% to 120% of its nominal value during production is merely one exemplary range believed sufficient to maintain the dose response curve within a desired range for certain methods of mass producing the inventive biosensors. One of skill in the art may wish to widen or narrow this range, depending upon the variations in dose response curve encountered in the particular manufacturing method in which these teachings are employed.

FIG. 3A illustrates the electrical pattern as it is initially formed on substrate 22, such as by laser ablation or other suitable means, as described above, whereas FIG. 3B shows the electrical pattern 50 after the adjustment to the area has been made. More specifically, the adjustment section 82 shown projected over a portion of adjustment fingers 54 in FIG. 3A represents a location where one or more of the adjustment fingers 54 can be severed, e.g., during a final stage of production. FIG. 3B shows the electrical pattern after three fingers 54 have been severed, in which a severed area 76 is formed where conductive material was removed. Thus, the effective area of the working electrode in this case has been reduced from about 120% of its nominal value to about 80% of its nominal value, since the sections of the three fingers 54 that extend upwardly and between the counter electrode have been electrically disconnected.

An access opening such as opening 44 shown in FIGS. 1 and 2 is provided in the covering layers directly over the adjustment section 82 so that the severing of fingers 54 as depicted in FIGS. 3A and 3B can be performed in a later stage of production. As just alluded, and as explained in further detail below, the number of adjustment fingers 54 that are to be severed, if any, is a design choice based upon the magnitude of the correction desired to be made to the dose-response curve of the particular biosensors being produced.

The embodiment shown in FIGS. 2 and 3A and 3B has certain advantages in that the wider fingers 53 are generally more robust than thinner fingers. Further, in this case, since fingers 53 define the outer edges of the working electrode, the gap widths between the top and bottom edges of the working electrode and the corresponding edges of the counter electrode remain the same irrespective of the number of fingers, if any, that are to be severed. This may be desirable in certain circumstances, as described below.

FIGS. 3C and 3D illustrate an alternate embodiment which differs from that of FIGS. 3A and 3B, in that the working electrode 157 includes only a single wider permanent finger 153 and three smaller fingers 154 that are selectively severable. In this case, the area of finger 153 may comprise, e.g., about 80% of the nominal value, whereas three fingers 154 combined may comprise an additional 40% of the nominal working electrode area. As with the embodiment shown in FIGS. 2, 3A and 3B, the gap width between the edges of the counter and working electrodes remains the same irrespective of the number of fingers, if any, that are to be severed. FIG. 3D illustrate all three fingers 154 being severed at severed area 76.

Figure 3F:
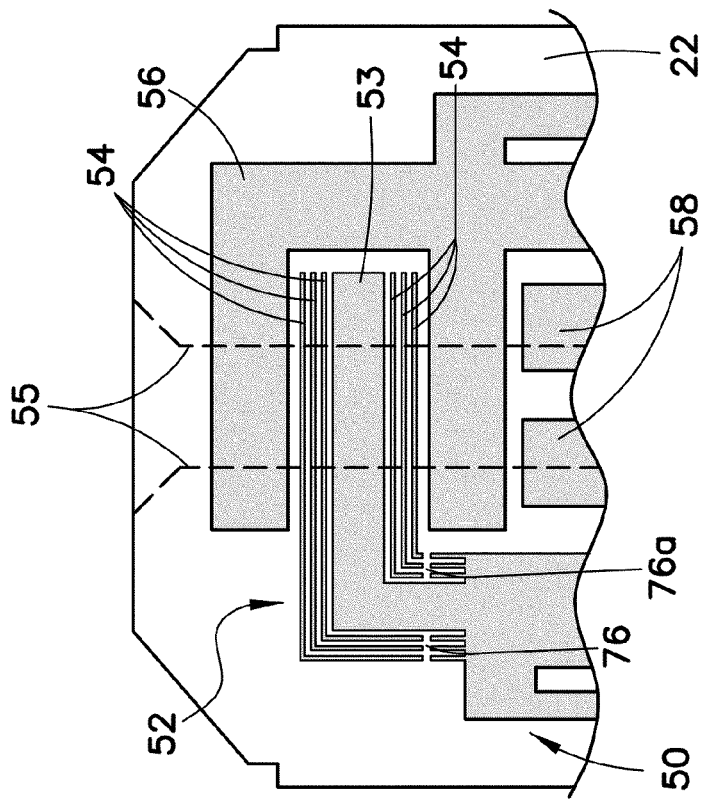
Figure 3E:
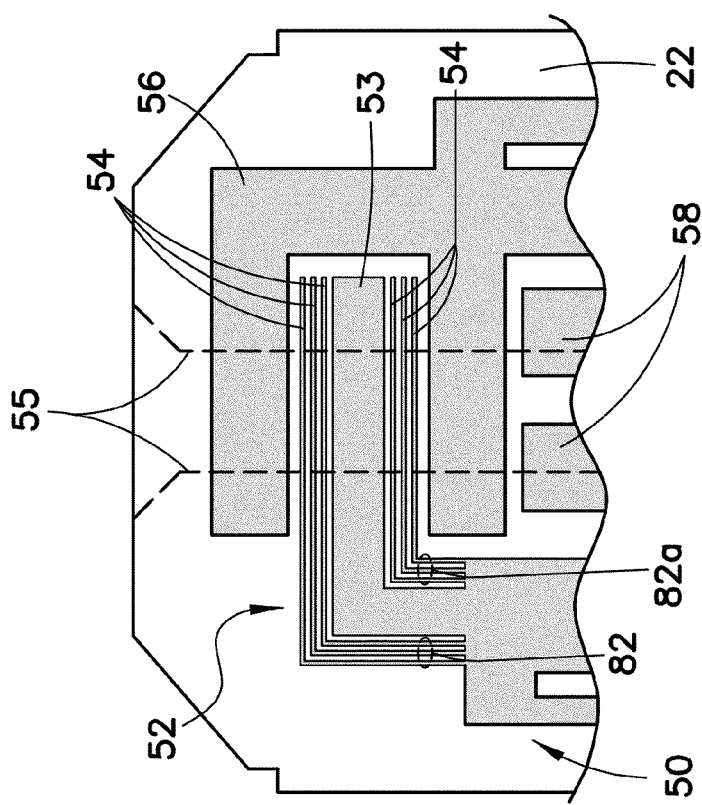

The working electrode of the embodiment shown in FIGS. 3E and 3F is somewhat the inverse of that shown in FIGS. 3A and 3B. In this case, there is a single wider permanent finger 53 centered between two sets of three smaller selectively severable fingers 54. This embodiment allows greater precision in adjustment due to there being two adjustment sections 82 and 82a, each of which allows severing zero to three fingers 54. FIG. 3F shows two severed areas 76 and 76a.

In FIGS. 3G and 3H, two sets of adjustment fingers 154 and 156 are provided in addition to permanent fingers 153. The fingers 154, 156 are separated by a space 150 therebetween. In addition to a first adjustment section 82 for severing fingers 154, a second adjustment section 84 shown in dashed lines in FIG. 3G is accessible by a cutting apparatus such as a laser. FIG. 3H illustrates an adjustment in which all adjustment fingers 154 and 156 have been severed, leaving severed areas 76, 86, but this of course need not be the case. Any number and combination of fingers 154 and 156 or none at all may be severed, depending upon the precise correction desired to be made to the dose-response curve.

FIGS. 3I and 3J illustrate another alternate embodiment in which the working electrode 157 is formed differently than working electrode 152 shown in FIGS. 3G and 3H. It has a connecting band 151 of conductive material disposed centrally with respect to the capillary channel 55 as illustrated. Two adjustment sections 82 and 84 are shown in FIG. 3I, and all selectively severable fingers are shown severed in severed areas 76 and 86 shown in FIG. 3J.

FIGS. 3K and 3L illustrate yet another embodiment of a dosing end 46 of a substrate 22 suitable for use in the system of biosensors in accordance with these teachings. In this case, working electrode 52 comprises a series of adjustment fingers 54, permanent fingers 53, a counter electrode 56, and dose sufficiency electrodes 58. One adjustment area 82 is provided as shown in FIG. 3K, and all fingers 54 are shown as being severed in severed area 76 shown in FIG. 3L.

In addition to removing material or severing it to reduce the effective area of the electrical pattern, conductive material may be instead added to an electrical pattern during biosensor production to electrically connect conductive material and thus increase the size of the effective area of the electrical pattern. For example, FIGS. 3M and 3N illustrate an embodiment in which the electrical pattern 50 is similar to that shown in FIGS. 3K and 3L, except that the electrical pattern 50 is initially formed with a severed area 76 (FIG. 3M), and during, e.g., a final stage of production, conductive material 90 is deposited through an access opening or window (such as opening 44 shown in FIGS. 1 and 2) and connects the fingers 54 as illustrated in FIG. 3N. The conductive material 90 may be deposited by any of a wide variety of methods known in the art. As another variation, a "plug" of conductive material may be provided in an access opening window such as opening 44 (FIG. 1) in a frictional fit and spaced away from the electrical pattern and substrate 22. This plug could then be tapped downward if desired during production to contact and thus electronically connect fingers 54. One of skill in the art would readily recognize any number of switching mechanisms that could be provided and activated during the production process to connect one or more adjustment fingers 54 as desired to adjust the effective area of the electrical pattern.

Figure 4:
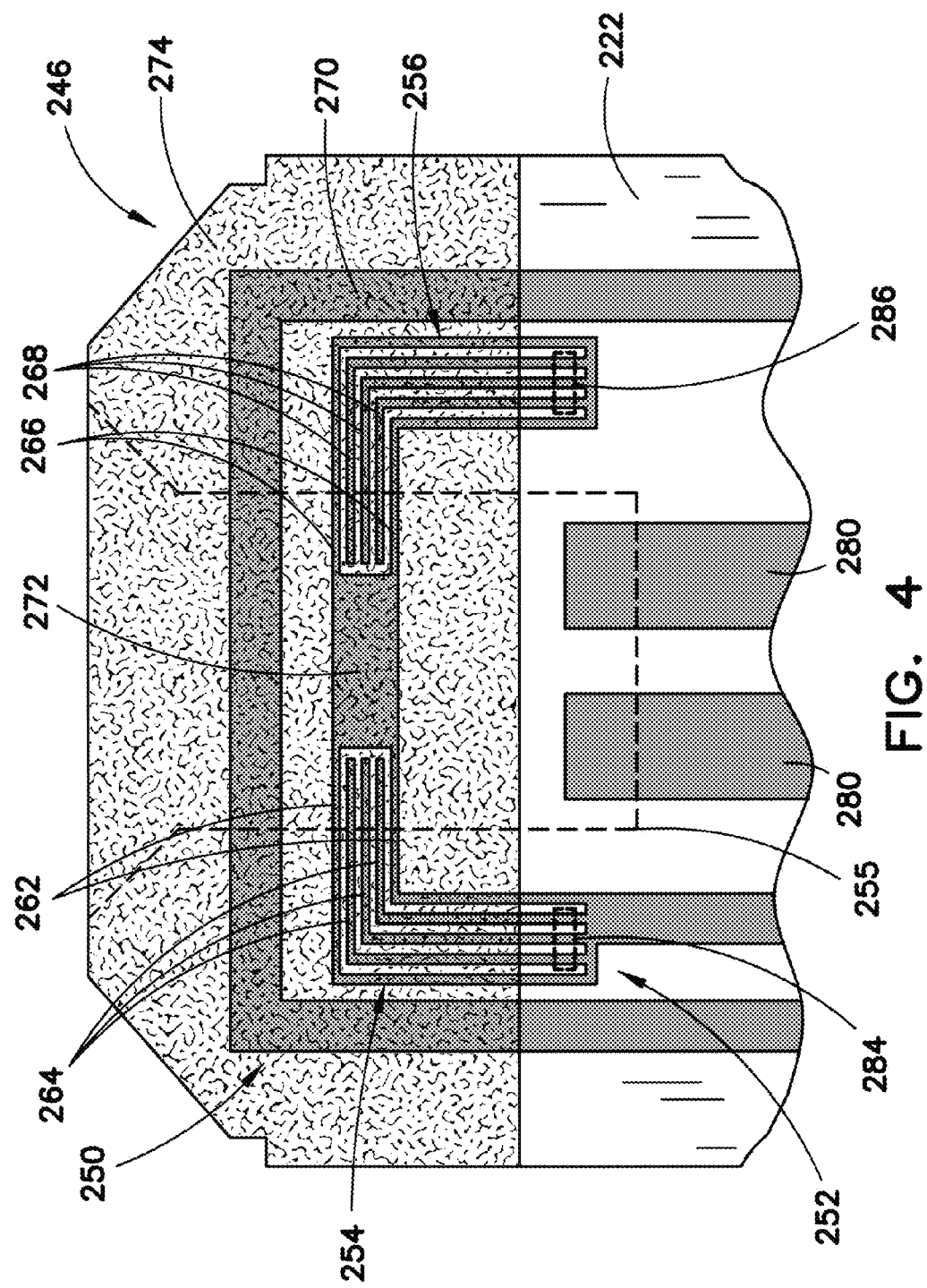
FIG. 4 is a fragmentary plan view of the dosing end of a biosensor substrate having an electrical pattern formed thereon whose working electrode effective area can be altered in accordance with these teachings.

Having set forth general examples of how the effective area of the electrical pattern may be varied, a more detailed example with numerical values is provided with respect to FIG. 4, which illustrates a dosing end 246 of a substrate 222 suitable for use in the system of biosensors in accordance with these teachings. An electrical pattern 250 is provided having a working electrode 252 that includes two multi-fingered sections 254 and 256. Section 254 includes permanent fingers 262 and adjustment fingers 264. Similarly, section 256 includes permanent fingers 266 and adjustment fingers 268. All adjustment fingers 264 and 268 are connected to the center part 272 of the working electrode 252 by means of the permanent fingers. A reagent film 274 (represented as a dot matrix) extends across the dosing end 246 of substrate 222, covering most of the counter electrode and working electrode. A counter electrode 270 and dose sufficiency electrodes 280 are also provided as shown, and a capillary boundary is shown in dashed lines as indicated by reference numeral 255. Of course, traces or leads extend from the working, counter, and dose sufficiency electrodes and terminate in contact pads that connect to a meter, as described above and shown in FIGS. 1A and 1B.

FIG. 4 also shows in dashed lines two adjustment windows 284 and 286 which represent windows such as access opening 44 (FIG. 1) through which the adjustment traces 264 and 268 could be accessed and severed if desired during production. Also, although the embodiment shown in FIG. 4 contemplates four permanent fingers, two each of fingers 262 and 268, a single permanent finger would be sufficient to ensure the basic function of the biosensor. However, in other cases it may be desirable to maintain a constant gap width between counter electrode 270 and working electrode 252 over the full width of the capillary channel, such as, e.g., if impedance measurements are used to correct for hematocrit or temperature, as is done in some biosensors that estimate glucose concentration in whole blood. See, e.g., U.S. Pat. No. 6,645,368, and U.S. Patent Application Serial Nos. 2004-0157337, 2004-0157338 and 2004-0157339. Permanent fingers 262 and 266 define the top edge of the working electrode as shown in FIG. 4 and accomplish the objective of maintaining constant gap width over the width of the capillary channel, if desired.

As also can be appreciated from FIG. 4, the adjustment windows 284 and 286 are located below and spaced away from the reagent film, which allows easier and more accurate severing of fingers 264 and 268, since they are not covered by the reagent film in the location shown and the latter thus does not interfere with cutting the fingers. Further, it may be desirable when, e.g., employing a laser to sever the fingers, to avoid illuminating the reagent since the laser light may undesirably affect the reagent chemistry. It is nonetheless possible to position the windows over the reagent film if desired in certain applications.

Table 1, below, provides examples of actual dimensions that are consistent with the formation of the electrical pattern shown in FIG. 4 by, e.g., a laser ablation process. As indicated by the examples, the overall length of the main working electrode area 272 across the capillary space 255 (e.g., from left to right in FIG. 4) is 1.15 mm and its overall width in the capillary space is 0.29 mm. The permanent fingers 262 and 268 are represented in Table 1 as two fingers with a width of 0.04 mm and a length of 0.35 mm located within the capillary and close to each side of the capillary boundary. There are six (6) adjustment fingers (three each of fingers 264 and 268) that are all represented the same in Table 1 since they are all substantially the same width and length.

The fifth column of Table 1 shows the sum total working electrode area, which increases proceeding down the column. For example, the total working electrode area attributed to area 272, and permanent fingers 262 and 266 is 0.362 mm$^2$.

Adding only one adjustment finger increases the area to 0.365 mm$^2$, whereas adding all six adjustment fingers brings the total area to 0.384 mm$^2$, as indicated in Table 1.

Table 1 is presented such that a configuration of electrical pattern 250 of FIG. 4 having three adjustment fingers (264 or 268) connected and the other three adjustment fingers severed or disconnected is established as a baseline nominal working electrode area of 100.0%. Thus, cutting all six fingers provides 97% of the nominal area and cutting none of the fingers provides 103% of the nominal area, as indicated. From equation (9), the resulting set of ΔA's are {−0.037, −0.024, −0.012, +0.012, +0.024, +0/037}.

TABLE 1

| Electrical Feature | Width* (mm) | Length* (mm) | Finger Area (mm$^2$) | ΣWE area (mm$^2$) | Effective Area Adjustment |
|---|---|---|---|---|---|
| Main working electrode (WE) | 0.29 | 1.15 | 0.33350 | | |
| WE permanent finger 1 | 0.04 | 0.35 | 0.01400 | | |
| WE permanent finger 2 | 0.04 | 0.35 | 0.01400 | 0.362 | 97.0% |
| WE adjustment finger 1 | 0.03 | 0.125 | 0.00375 | 0.365 | 98.0% |
| WE adjustment finger 2 | 0.03 | 0.125 | 0.00375 | 0.369 | 99.0% |
| WE adjustment finger 3 | 0.03 | 0.125 | 0.00375 | 0.373 | 100.0% |
| WE adjustment finger 4 | 0.03 | 0.125 | 0.00375 | 0.377 | 101.0% |
| WE adjustment finger 5 | 0.03 | 0.125 | 0.00375 | 0.380 | 102.0% |
| WE adjustment finger 6 | 0.03 | 0.125 | 0.00375 | 0.384 | 103.0% |

*in capillary space

Table 1 illustrates adjusting the effective area in 1% increments. However, in another embodiment, the working electrode effective area could be provided in increments of −9%, −6%, −3%, nominal, +3%, +6% and +9% by the adjustment finger arrangement just noted or other adjustment arrangements disclosed above. One of skill in the art could provide other increments and combinations thereof to meet the system drift that is contemplated or encountered in a particular manufacturing process.

Figure 5:
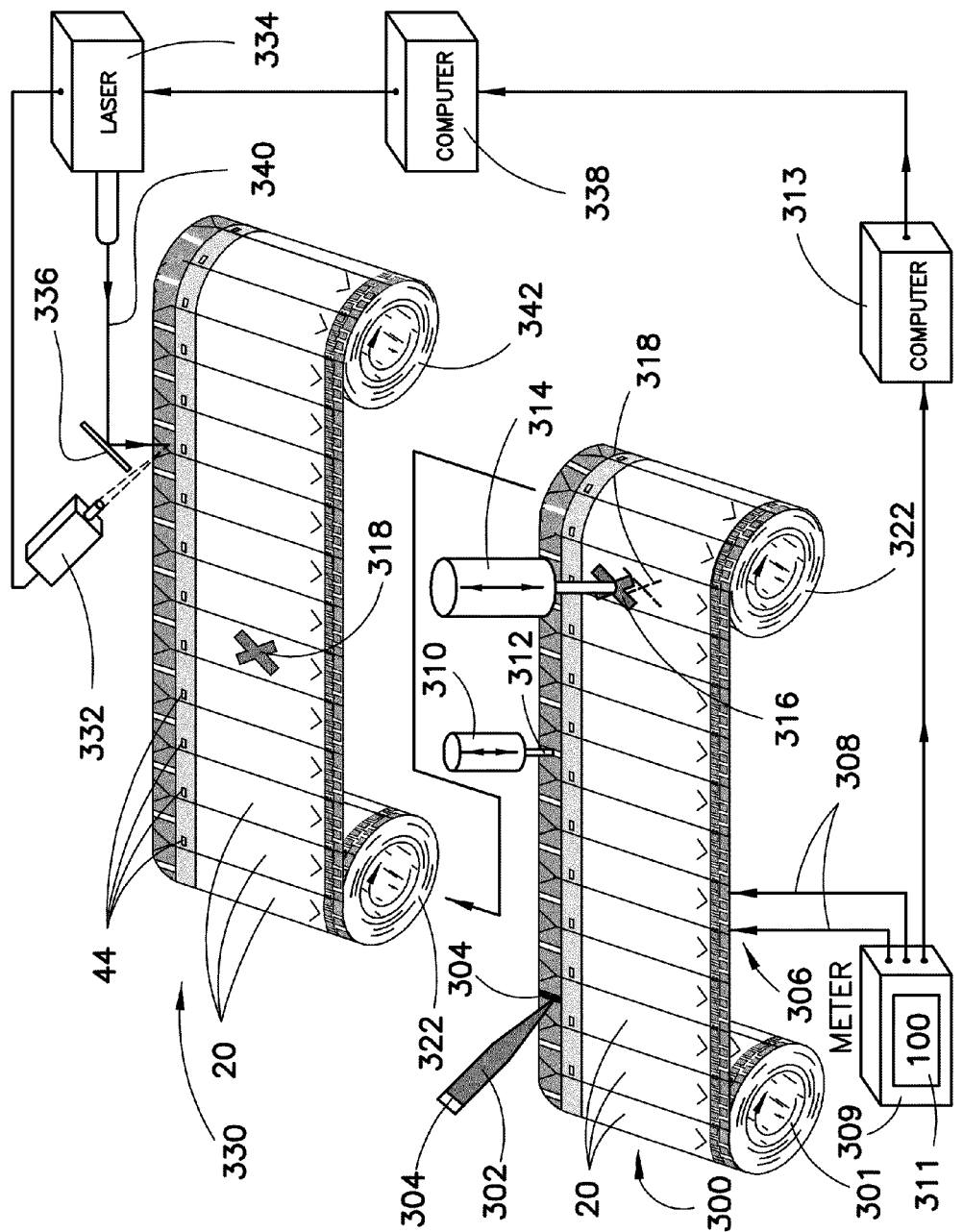
FIG. 5 is a perspective view shown partially schematically illustrating a production method of biosensors in accordance with these teachings.

Turning now to FIG. 5, an exemplary method of manufacturing biosensors in accordance with these teachings is illustrated. A first line or production station of biosensors 300 includes a roll 301 of biosensors 20 provided in a reel to be unwound as indicated. Biosensors 20 on roll 301 are substantially as described above with reference to FIGS. 1 and 2, except the biosensors are provided in a continuous web and have not yet been trimmed and cut into individual biosensors, which occurs as a final stage of production. As roll 301 is unwound, a dispenser 302 containing aqueous quality control ("QC") solution 304, e.g., a calibrator solution, doses selected ones of the biosensors 20 with QC solution 304. As shown, the QC solution is drawn into the sample receiving chamber of the selected biosensor.

In the process illustrated in FIG. 5, the roll may stop momentarily while dispenser 302 quickly doses the biosensor, or the roll may move continuously. As the selected biosensor 20 moves, the chemical and physical processes quickly take place in chamber 34. The selected biosensor 20 is advanced to a testing station 306 and then contacted by probes 308, which are shown in FIG. 5 contacting a biosensor 20 that is shown located in FIG. 5 three biosensors ahead of the selected biosensor in the line. A meter or measurement device 309 having an optional display 311 provides an excitation sequence to the selected biosensors 20 through probes 308 and records the response signal. Computing device 313 receives and records the response for all biosensors that are tested in a roll or multiple rolls and calculates the desired correction to be made in the effective area of the electrical patterns.

Positioned three biosensors ahead of the testing station 306 in line 300 is a wicking station 310 which can reciprocate as depicted by an arrow and includes a wick element 312 that contacts the dosing end of the selected biosensor and draws the QC solution 304 therefrom.

Finally, positioned another four biosensors forward in the line is a reciprocably mounted marking station 314 having a marker or stamp 316 shown in the shape of an "X" that imprints a reject mark 318 on those biosensors that have been selected for testing. Reject mark 318 is shown in phantom in line 300 since the biosensor shown positioned under station 314 has not been dosed and therefore would not actually be marked with an "X." The ratio of biosensors tested to total produced in the production line is a design variable, but it is envisioned that many may be tested. In one embodiment of this design variable, an entire vial of 50 strips is tested periodically during production. For example, in a reel-to-reel based manufacturing process such as is employed in making ACCU-CHEK® Aviva test strips, there are typically about 111 strips per meter, and 50 strips are selected for testing about every 200 meters. Thus, the ratio is about 1 strip selected for testing per every 445 strips that are produced. The optimum ratio depends in many respects upon the reproducibility of each lot of reagent produced as well as the reproducibility of applying the reagent layer film on the dosing end 46 of substrate 22. The greater the combined reproducibility, the higher the ratio of tested strips to strips produced. Although the testing is destructive, the small ratio of tested biosensors that are discarded per total produced does not significantly increase production costs, and is indeed more than offset by obviating prior art solutions such as providing ROM keys, bar codes and the like.

With further reference to FIG. 5, after selected ones of the biosensors 20 are dosed, tested, wicked and marked, they are wound up in a second roll 322 to be further processed in line 330. Line or station 330 includes a camera 332, a laser 334 and an optical arrangement shown schematically with a mirror 336. Laser 334 has a computer or computing/machine control system 338 associated therewith that receives the calculated area correction of, e.g., the working electrodes of the electrical patterns, from the first computer 313.

Camera 332 is used in conjunction with system 338 to allow the laser to cut as required to adjust the area of the working electrode of all biosensors in line 330. More particularly, as line 330 advances biosensors 20 from left to right as illustrated, laser 334 pulses beams 340 that are reflected by mirror 336 and projected through windows or access openings 44 and, e.g., makes a cut like that described with reference to FIGS. 3A and 3B, above, to produce severed area 76 as needed. The optical result read by the camera is processed by the computing system 338 to ensure that the laser is properly making the required cuts in the area designated. After this adjustment is made, the biosensors are rewound onto roll 342 for further processing, during which the biosensors are, e.g., separated from the roll, trimmed and packaged in vials. Details of the further processing of the type just noted to complete strip assembly are provided in U.S. Publication No. 20050013731, the entire disclosure of which is incorporated herein by reference.

While one method of production is illustrated in FIG. 5, one of skill in the art would readily recognize many variations. For example, while two separate stations 300 and 330 are shown in FIG. 5, the functions of these two stations could feasibly be combined in a single, albeit longer line. In other words, line 300 could be lengthened and laser 334 and camera 332 could be positioned downstream of the marking station 314 in this single line. Furthermore, line 300 depicts the dosing, testing, wicking and marking stations spaced apart along the line such that the line can continually move while selected biosensors are tested. However, if desired, these stations could be positioned all together and the line could be periodically stopped when one of the biosensors is to be tested. When only few of the biosensors are to be tested, this option may be more desirable in terms of setting up the line. Furthermore, the line could be stopped and the testing could be done manually by, e.g., a technician trained for such purpose. One of skill in the art would recognize various other options for incorporating these teachings into the production of biosensors.

Figure 6A:
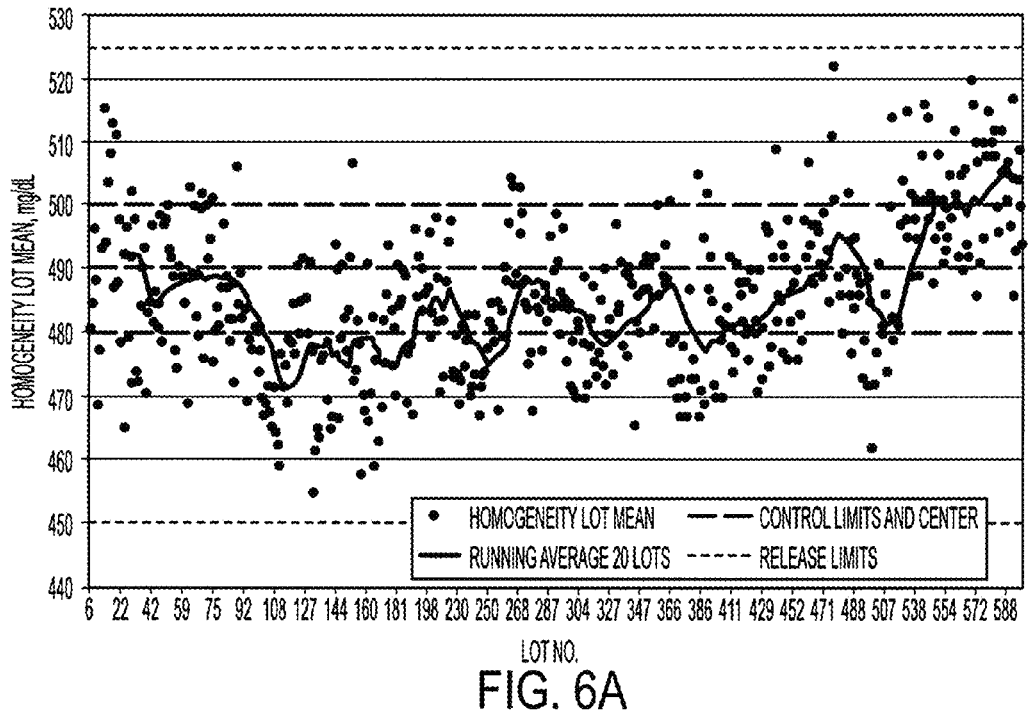
FIGS. 6A and 6B are graphs that illustrate a method of prospectively maintaining the dose-response curve of biosensors within a predetermined range.

A second aspect of these teachings enables the biosensors to be adjusted for an accurate estimation of analyte concentration by prospectively predicting using statistical process control (SPC) the adjustment needed of the area of the electrical pattern of biosensors that have not yet been produced. To illustrate this inventive aspect, FIG. 6A shows an average biosensor response to an aqueous control solution per lot (referred to as "homogeneity lot mean") for several production lots. Homogeneity lot mean is determined by a protocol that involves statistical sampling of biosensors from multiple rolls that form the production lot. Also shown in FIG. 6A are release limits above and below which a lot is typically discarded as insufficient even for use in systems employing complex correction algorithms. Also shown are theoretical control limits and center lines, the theoretical control limits representing the predetermined range or tolerance within which the response of the biosensors is desired to be maintained. The running average is plotted as a solid black line.

As can be appreciated from the illustrated results in FIG. 6A, the average homogeneity lot mean (solid line) dips below the lower control limit starting with approximately lot 102, and then crosses over and below the lower control limit six (6) more times before finally crossing the upper control limit at about lot 540. These trends can be monitored and prospective corrections can be implemented with SPC.

Figure 6B:
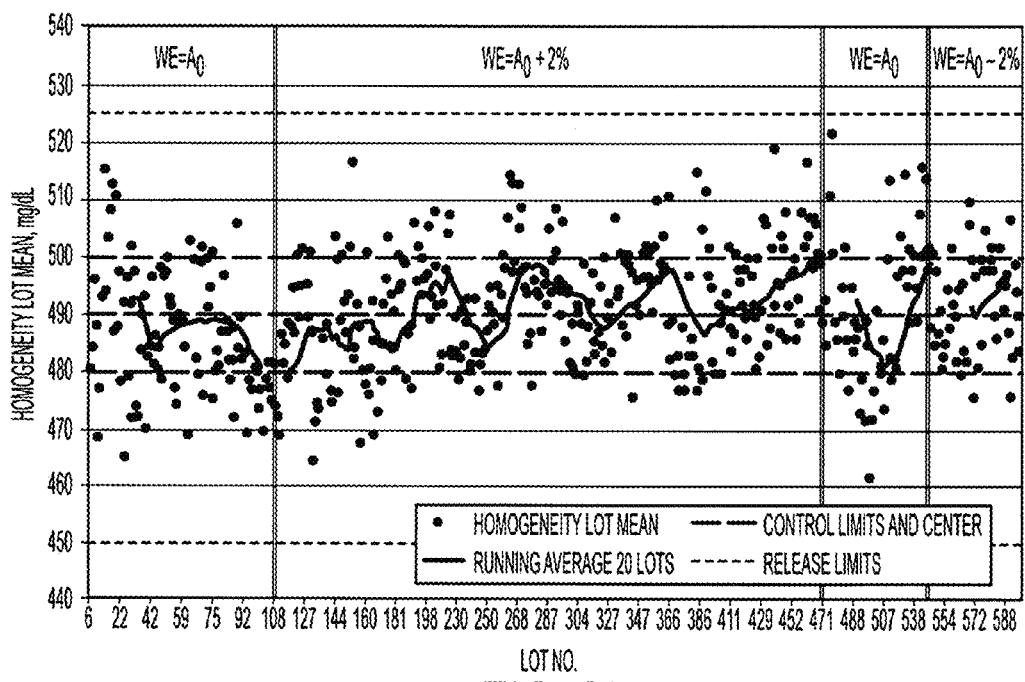

Specifically, FIG. 6B shows the expected homogeneity lot means if a working electrode area correction made in accordance with the above teachings were to be employed. The nominal (no correction) working electrode area $A_o$ is used for all lots up to lot 102. At this point, as discussed above, the lower threshold is crossed and the working electrode area for subsequent lots is then adjusted to ($A_o$+2%) as indicated in FIG. 6B. As can be appreciated, by maintaining the working electrode area at a value of ($A_o$+2%), the homogeneity lot mean shown in the solid line is maintained between the upper and lower control limits for hundreds of subsequent lots, which was not the case depicted in FIG. 6A without the area adjustment. At lot 472, the upper SPC control limit is crossed. To compensate for this, biosensors of subsequent lots have their working electrode areas brought back to $A_o$. After the upper SPC control limit is crossed again at lot 540, the working electrode area of the biosensors is changed to ($A_o$−2%) as indicated in FIG. 6B.

Figure 7:
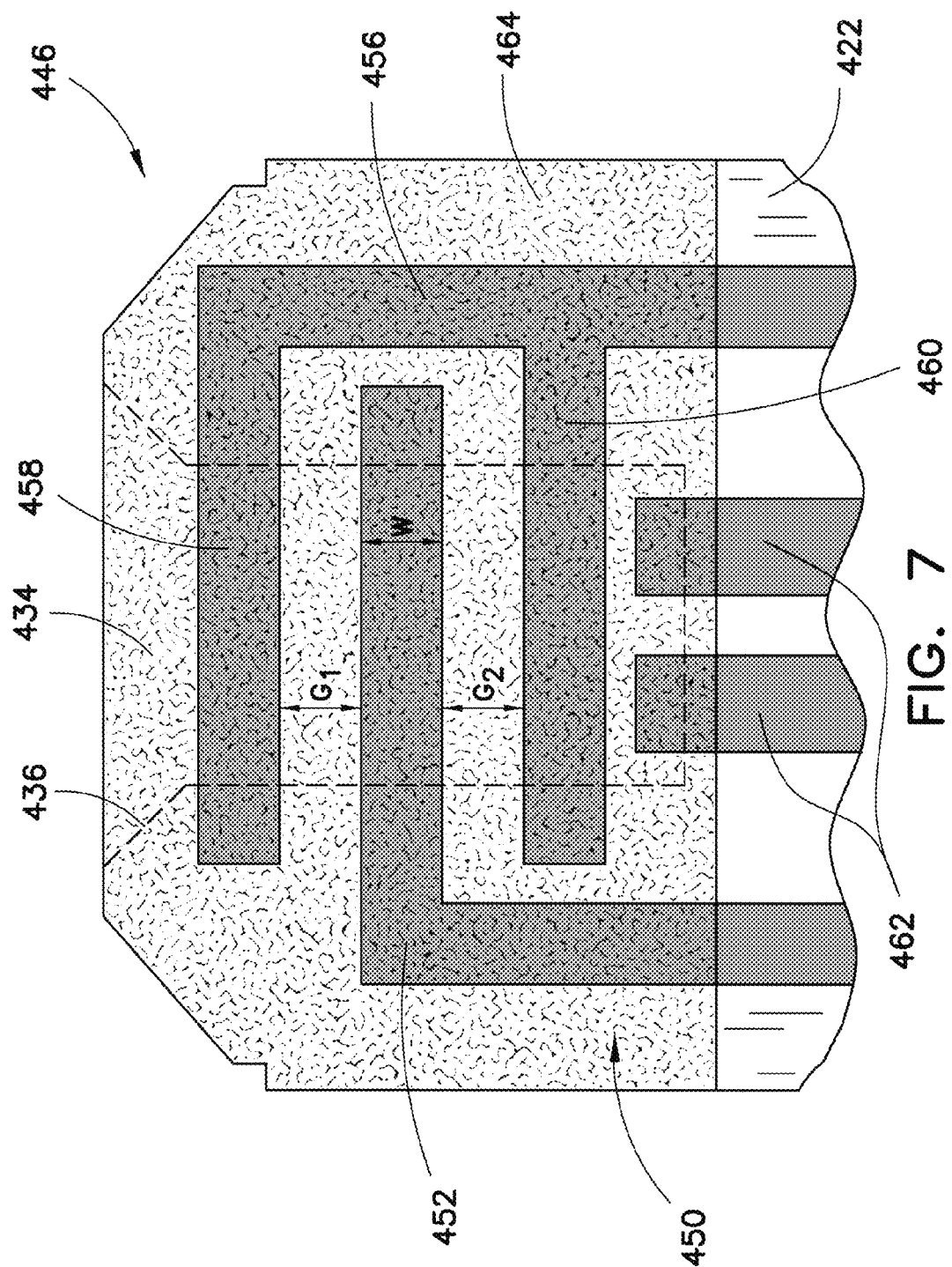
FIG. 7 is a fragmentary plan view of the dosing end of a biosensor substrate having an electrical pattern formed thereon whose working electrode effective area can be sized in accordance with these teachings to prospectively maintain the dose-response curves of the biosensors within a predetermined range.

As alluded above, since the correction is prospective, it can be built into an earlier stage of the manufacturing process of the biosensors, if desired, which may offer certain advantages in terms of economies of production and ease of implementation. FIG. 7 illustrates a dosing end 446 of a substrate 422 suitable for employing the prospective corrections described with reference to FIG. 6B. An electrical pattern 450 is provided having a working electrode 452, a counter electrode 456 having two fingers or segments 458 and 460, and dose sufficiency electrodes 462. The electrical pattern 450 can be formed from laser ablation, laser scribing, screen printing or other known techniques known in the art to produce electrical patterns on a biosensor substrate(s). The capillary space or sample receiving chamber 434 is delineated by boundary 436 shown as a dashed line. A reagent film or layer 464 covers the electrodes.

The working electrode 452 has a width "W" as indicated, whereas the gaps between working electrode 452 and segments 458 and 460 are denoted $G_1$ and $G_2$, respectively. Tables 2, 3 and 4 illustrate three different options for adjusting the area of the working electrode in combination with various gap width changes.

Table 2, below, illustrates an option in which gaps $G_1$ and $G_2$ are maintained while the width W of working electrode 452 is varied.

TABLE 2

| WE area, mm² | Δ WE area | W (mm) | $G_1$ (mm) | $G_2$ (mm) |
|---|---|---|---|---|
| 0.390 | +4% | 0.260 | 0.255 | 0.255 |
| 0.383 | +2 | 0.255 | 0.255 | 0.255 |
| 0.375 | 0% | 0.250 | 0.255 | 0.255 |
| 0.368 | −2% | 0.245 | 0.255 | 0.255 |
| 0.360 | −4% | 0.240 | 0.255 | 0.255 |

Table 3 provides an option in which the width W of the working electrode as well the gap $G_2$ between working electrode 452 and segment 460 of the counter electrode are varied. By contrast $G_1$ is maintained constant, which may have certain advantages in terms of reliably and reproducibly detecting sample entering the sample receiving chamber 434.

TABLE 3

| WE area, mm² | Δ WE area | W (mm) | $G_1$ (mm) | $G_2$ (mm) |
|---|---|---|---|---|
| 0.390 | +4% | 0.260 | 0.255 | 0.245 |
| 0.383 | +2 | 0.255 | 0.255 | 0.250 |
| 0.375 | 0% | 0.250 | 0.255 | 0.255 |
| 0.368 | −2% | 0.245 | 0.255 | 0.260 |
| 0.360 | −4% | 0.240 | 0.255 | 0.265 |

Table 4, below, illustrates an option in which the working electrode width W and the gaps $G_1$ and $G_2$ are varied symmetrically, which maintains a constant measurement volume, which may have certain advantages when using these teachings for, e.g., coulometric measurements.

TABLE 4

| WE area, mm² | Δ WE area | W (mm) | $G_1$ (mm) | $G_2$ (mm) |
|---|---|---|---|---|
| 0.390 | +4% | 0.265 | 0.250 | 0.250 |
| 0.383 | +2 | 0.260 | 0.252 | 0.252 |
| 0.375 | 0% | 0.255 | 0.255 | 0.255 |
| 0.368 | −2% | 0.250 | 0.258 | 0.258 |
| 0.360 | −4% | 0.245 | 0.260 | 0.260 |

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of manufacturing electrochemical biosensors of the same model, comprising:
    (a) producing a first biosensor having a first electrical pattern with a first effective area;
    (b) determining a dose-response curve of the first biosensor;
    (c) using the dose-response curve determined for the first biosensor to predict a second effective area for a second electrical pattern of a second biosensor before the second biosensor is made, the second effective area being different from the first effective area; and
    (d) forming the second biosensor, the second effective area being obtained during initial formation of the second electrical pattern, wherein the second biosensor has a dose-response curve that is within a desired predetermined range.

2. The method of claim 1, wherein step (a) comprises forming a first working electrode of the first biosensor with a first width and step (d) comprises forming a second working electrode of the second biosensor with a second width that is different from the first width.

3. The method of claim 2, wherein step (a) comprises forming the first working electrode and a first counter electrode with a gap therebetween and step (d) comprises maintaining the same size of the gap in the second biosensor.

4. The method of claim 2, wherein step (a) comprises forming the first working electrode and a first counter electrode with a first gap therebetween and step (d) comprises forming the second working electrode and a second counter electrode with a second gap therebetween, the second gap having a different size than the first gap.

5. The method of claim 1, wherein:
    the first biosensor comprises a plurality of first biosensors;
    the dose-response curve determined in step (b) comprises an average dose-response curve of the plurality of first biosensors; and
    the second biosensor comprises a plurality of second biosensors.

6. The method of claim 5, further comprising:
    determining an average dose-response curve of the plurality of second biosensors;
    predicting a third effective area for a third electrical pattern for a plurality of third biosensors before the third biosensors are made, the third effective area being different from the second effective area; and
    forming the plurality of third biosensors with the third electrical patterns having the third effective area, wherein the plurality of third biosensors has a dose-response curve that is within the desired predetermined range.

7. The method of claim 6, wherein the first and third effective areas are the same.

8. The method of claim 5, wherein the plurality of first biosensors comprises a first production lot of biosensors and the plurality of second biosensors comprises a second production lot of biosensors.

9. The method of claim 5, further comprising establishing upper and lower control limits which define the desired predetermined range.

\* \* \* \* \*